United States Patent

Pollard et al.

(10) Patent No.: US 7,572,011 B2
(45) Date of Patent: Aug. 11, 2009

(54) CONTACT LENSES FOR USE IN MOTION CAPTURE

(75) Inventors: Brad Pollard, San Diego, CA (US); Gary M. Zalewski, Oakland, CA (US)

(73) Assignee: Sony Computer Entertainment America Inc., Foster City, CA (US)

( * ) Notice: Subject to any disclaimer, the term of this patent is extended or adjusted under 35 U.S.C. 154(b) by 68 days.

(21) Appl. No.: 11/460,611

(22) Filed: Jul. 27, 2006

(65) Prior Publication Data

US 2008/0024722 A1    Jan. 31, 2008

(51) Int. Cl.
*A61B 3/14* (2006.01)
*G02C 7/04* (2006.01)

(52) U.S. Cl. .................... 351/209; 351/162

(58) Field of Classification Search .............. 351/209, 351/200, 205, 159, 160 R, 162, 163, 165
See application file for complete search history.

(56) References Cited

U.S. PATENT DOCUMENTS 3,804,496 A * 4/1974 Crane et al. ................ 351/210
6,152,564 A * 11/2000 Ober et al. ................. 351/210
7,021,761 B2 * 4/2006 Kunzler et al. ............. 351/162
2007/0121065 A1 * 5/2007 Cox et al. ................... 351/209

OTHER PUBLICATIONS

Wikipedia, Motion Capture, online article: http://en.wikipedia.org/wiki/Motion_capture. first printed Jul. 13, 2006, 6 pages.
Patent Cooperation Treaty; "Notification of Transmittal of the International Search Report and the Written Opinion of the International Searching Authority or the Declaration" issued in corresponding PCT/US07/72584; mailed Aug. 27, 2008; 2 pages (86355PC).
Patent Cooperation Treaty; "International Search Report" issued in corresponding PCT/US07/72584; mailed Aug. 27, 2008; 2 pages (86355PC).
Patent Cooperation Treaty; "Written Opinion of the International Searching Authority" issued in corresponding PCT/US07/72584; mailed Aug. 27, 2008; 3 pages (86355PC).

* cited by examiner

*Primary Examiner*—William C Choi
*Assistant Examiner*—Jack Dinh
(74) *Attorney, Agent, or Firm*—Fitch, Even, Tabin & Flannery

(57) ABSTRACT

An apparatus for use in motion capture includes a contact lens and a tracking feature incorporated into the contact lens. A method for use in motion capture includes inserting a contact lens having a tracking feature into a performer's eye and tracking movements of the performer's eye using the tracking feature.

5 Claims, 2 Drawing Sheets

CONTACT LENSES FOR USE IN MOTION CAPTURE

BACKGROUND OF THE INVENTION

1. Field of the Invention

The present invention relates generally to computer animation, and more specifically to motion capture techniques.

2. Discussion of the Related Art

Motion capture, or "mocap," is a technique of digitally recording the movements of real things, such as humans, as a source of motion data for computer animation. The technique involves a performer wearing a set of markers that are tracked by sensors as the performer moves. A computer records the movements to provide a digital representation of the motion. The digital representation of the motion can then be used in animation so that an animator does not have to draw each frame.

It is with respect to these and other background information factors that the present invention has evolved.

SUMMARY OF THE INVENTION

One embodiment provides an apparatus for use in motion capture, comprising: a contact lens; and a tracking feature incorporated into the contact lens.

Another embodiment provides a method for use in motion capture, comprising the steps of: inserting a contact lens having a tracking feature into a performer's eye; and tracking movements of the performer's eye using the tracking feature.

A better understanding of the features and advantages of various embodiments of the present invention will be obtained by reference to the following detailed description and accompanying drawings which set forth an illustrative embodiment in which principles of embodiments of the invention are utilized.

BRIEF DESCRIPTION OF THE DRAWINGS

The above and other aspects, features and advantages of embodiments of the present invention will be more apparent from the following more particular description thereof, presented in conjunction with the following drawings wherein.

DETAILED DESCRIPTION

Further to the above discussion, motion capture or tracking has expanded into education, training, sports and recently computer animation for cinema and video games. A performer wears reflective markers near each joint to identify the motion by the positions or angles between the markers. Reflective markers are tracked, optimally at least two times the rate of the desired motion, to submillimeter positions. The motion capture computer software records the positions, angles, velocities, accelerations and impulses, providing an accurate digital representation of the motion.

In entertainment applications this can reduce the costs of animation which otherwise requires the animator to draw each frame, or with more sophisticated software, key frames which are interpolated by the software. Motion capture saves time and creates more natural movements than manual animation, but is limited to motions that are anatomically possible. Some applications might require additional impossible movements like animated super hero martial arts or stretching and squishing that are not possible with real actors.

Optical systems triangulate the three dimensional (3D) position of a marker between a number of cameras calibrated to provide overlapping projections. Tracking a large number of markers or multiple performers or expanding the capture area is accomplished by the addition of more cameras. These systems produce data with three degrees of freedom for each marker, and rotational information must be inferred from the relative orientation of three or more markers. For example, shoulder, elbow and wrist markers may be used to provide the angle of the elbow.

The features on a character's face are some of the most difficult parts of the character to animate. And perhaps the character's eyes are the most difficult. The difficulty of animating a character's eyes can lead to the problem of characters having so-called "dead eyes" in video games and other computer animations.

The look of the character's face can be greatly improved by creating realistic eye movement. But creating realistic eye movement is difficult because eye and eyelid animation is complex. Namely, such animation seeks to combine several different movements, such as voluntary movements (e.g. the point of focus of the character's eyes), involuntary movements (e.g. the character's facial expression), and automatic movements (e.g. blinking of the eyes).

As of today, motion capture markers have been limited to faces, hands and body parts. Animators have still had to animate eye movement manually. Embodiments of the present invention provide contact lenses that include a tracking feature for use in motion capture of eye movements. Namely, such contact lenses may be worn by the performer during the motion capture process to track the movements of the performer's eyes.

Figure 1:
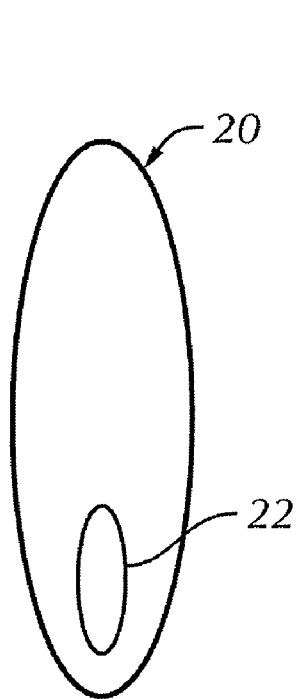
FIG. 1 illustrates an apparatus made in accordance with an embodiment of the present invention.

Referring to FIG. 1, there is illustrated an optical contact lens 20 made in accordance with an embodiment of the present invention. The optical contact lens 20, which may be used in motion capture, includes a tracking feature incorporated into the contact lens. In this example, the optical contact lens 20 includes a reflector or reflective dot 22 embedded therein. The reflective dot 22 comprises a tracking feature and may be used as a marker in the motion capture process. The reflective dot 22 may comprise a reflective material. In other embodiments the reflective dot 22 may comprise many different shapes.

Figure 2:
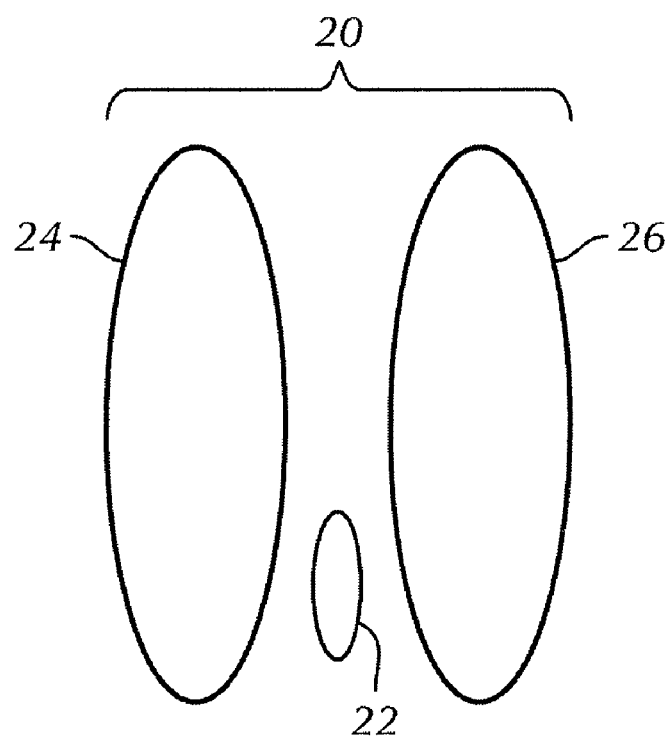
FIG. 2 is an exploded view of the apparatus shown in FIG. 1 illustrating an assembly thereof in accordance with an embodiment of the present invention.

FIG. 2 shows an exploded view of the optical contact lens 20 and illustrates one manner in which it may be assembled in accordance with an embodiment of the present invention. Specifically, the reflective dot 22 may be embedded between two layers of plastic or contact lens material 24, 26. By way of example, in some embodiments a typical construction may comprise 45% methafilcon B, and 55% water in a buffered 0.9% saline solution.

Figure 3:
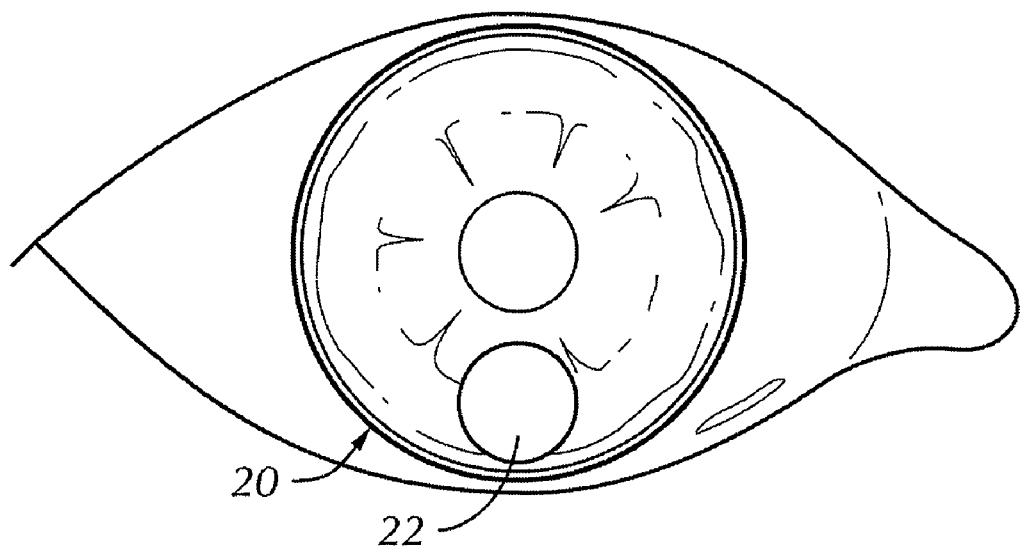
FIG. 3 illustrates the apparatus shown in FIG. 1 inserted in a person's eye in accordance with an embodiment of the present invention.

FIG. 3 illustrates the optical contact lens 20 being worn in a user's eye. The weight of the reflective dot 22 will naturally and automatically center itself at the bottom of the iris, allowing the user to see clearly out into space. Offsets may then be calculated at the time of, or after, the motion capture process so that the reflective dot 22 appears in the actual center of the eye. In some embodiments a pair of the optical contact lenses 20 may be ordered to fit a specific user, and in some embodiments they may even contain corrective prescriptions.

Thus, some embodiments of the present invention provide for a reflective material that consistently rests near the bottom of iris. If needed, bright lights may be used with the camera set-up during the motion capture process to reduce dilation of the pupils. Such bright light can cause the pupils to tighten up nicely.

In the illustrated embodiment the reflective dot 22 comprises the tracking feature of the contact lens 20 and may be used as a marker in motion capture. It should be well understood, however, that in other embodiments the tracking feature may comprise many different shapes or patterns, or the tracking feature may comprise any other machine recognizable feature.

Furthermore, the tracking feature may occupy any portion or all of the lens. For example, depending on the configuration, the location of the tracking feature may be at the bottom of the iris as shown, or outside the iris, or across a larger portion of the lens, or some combination thereof.

In other embodiments, the tracking feature may be visually blocking/opaque, dithered to enable partial transparency to allow the user to see, or a combination thereof. For example, a combination opaque and transparent lens may be optimized so that the portion over the iris is less opaque but the region around the iris gets increasingly opaque.

In other embodiments, the tracking feature may comprise multiple colors. For example, the tracking feature may comprise a color different than the rest of the contact lens. As another example, the colors may be disposed in sectors and wedges. Each such wedge may have a different color than its neighboring wedge, each sector may have a different color than its neighboring sector, etc. In some embodiments the colors may be chosen so that each neighbor has a high contrast color from its other neighbors (e.g. neon orange vs. neon green) to yield maximum contrast between color regions.

Figure 4:
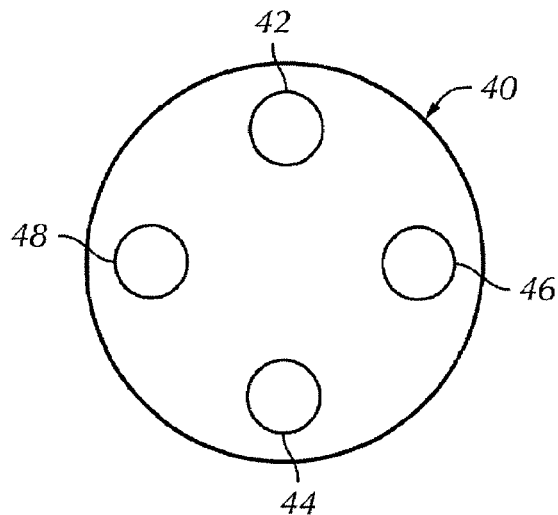
FIG. 4 illustrates an apparatus made in accordance with another embodiment of the present invention.

Referring to FIG. 4, there is illustrated a contact lens 40 made in accordance with another embodiment of the present invention. In this embodiment the tracking feature comprises four dots 42, 44, 46, 48, which are arranged in a north, south, east, west pattern. Such a pattern allows for tracking of the eye at its extreme left, right, up or down, or at any radian of rotation, where one or more of the dots 42, 44, 46, 48 might become covered up by the eye lid or surrounding skin. While four dots are illustrated it should be well understood that any number of dots may be used and that instead of dots the tracking feature may comprise any other shape or pattern. Furthermore, the dots 42, 44, 46, 48 may all be the same color, different colors, or some the same color and some a different color.

Figure 5:
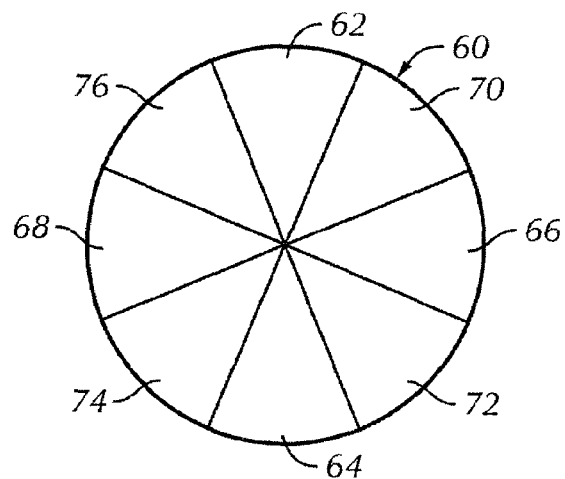
FIG. 5 illustrates an apparatus made in accordance with another embodiment of the present invention.

FIG. 5 illustrates a contact lens 60 made in accordance with yet another embodiment of the present invention. In this embodiment the tracking feature comprises eight regions 62, 64, 66, 68, 70, 72, 74, 76 which are arranged in a north, south, east, west, northeast, southeast, southwest, northwest pattern. Similar to above, such a pattern allows for tracking of the eye at its extreme left, right, up or down, or at any radian of rotation, where one or more of the regions 62, 64, 66, 68, 70, 72, 74, 76 might become covered up by the eye lid or surrounding skin. While eight regions are illustrated it should be well understood that any number of regions may be used and that instead of wedge shapes the tracking feature may comprise any other shape or pattern. Furthermore, the regions 62, 64, 66, 68, 70, 72, 74, 76 may all be the same color, different colors, or some the same color and some a different color.

Thus, in accordance with various embodiments of the present invention, transparent, semi-transparent, or even opaque motion capture contact lenses include a tracking feature. The tracking feature may comprise one or more specific colors or colors in combination with a shape or pattern target marking. The tracking feature may include any shape, pattern or arrangement that is trackable or detectable by a motion capture system so that eye movement may be tracked. The use of such lenses to capture eye movements in a motion capture process can be used to reduce the problem of "dead eye" in video games and other animations.

Figure 6:
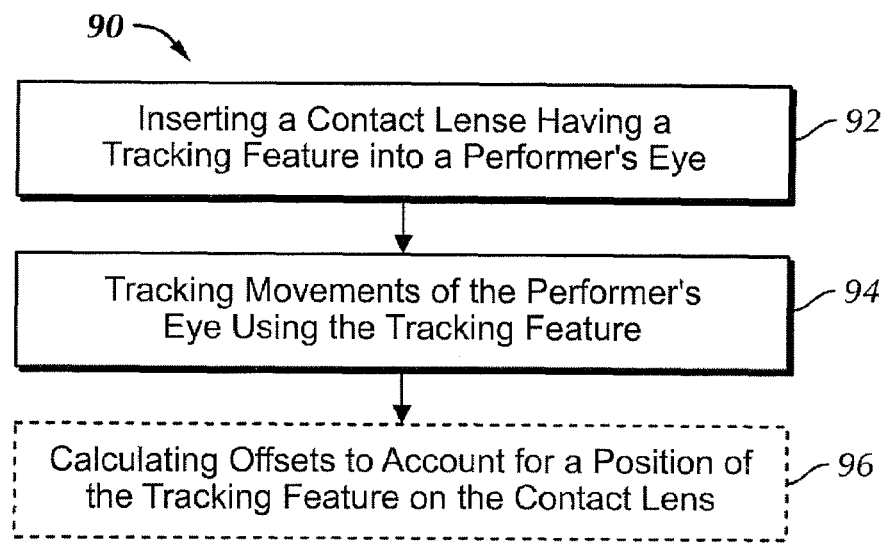
FIG. 6 is a flow diagram illustrating a method for use in motion capture in accordance with an embodiment of the present invention.

Referring to FIG. 6, there is illustrated a method 90 in accordance with an embodiment of the present invention. The method 90 may be used in motion capture processes, such as for use in making video games and other animations. In step 92 a contact lens having a tracking feature is inserted into a performer's eye. The performer then moves in some manner. In step 94 the movements of the performer's eye are tracked using the tracking feature.

In step 96, which is an optional step as indicated by the dashed lines, offsets may be calculated to account for the positioning of the tracking feature on the contact lens. For example, if the tracking feature comprises an off center reflective dot as shown in FIGS. 1-3, an offset may be calculated to account for the dot not being centered. Such calculation may be performed by any type of computer system or the like.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for use in motion capture, comprising:
   a contact lens; and
   a tracking feature incorporated into the contact lens;
   wherein the tracking feature is patterned into two or more regions and arranged to allow tracking of an eye based on tracking of at least one said region in the pattern; and
   wherein the tracking feature comprises a reflective dot.

2. An apparatus in accordance with claim 1, wherein the contact lens comprises two layers of material.

3. An apparatus in accordance with claim 2, wherein the tracking feature is embedded between the two layers of material.

4. An apparatus in accordance with claim 1, wherein the tracking feature comprises a shape.

5. An apparatus in accordance with claim 1, wherein the tracking feature comprises a color different than the rest of the contact lens.

* * * * *